(12) United States Patent  (10) Patent No.: US 7,501,198 B2
Barlev et al.  (45) Date of Patent: Mar. 10, 2009

(54) STERILE TRANSFER BATTERY CONTAINER

(75) Inventors: B. Alex Barlev, Largo, FL (US); Walton Lane Ector, Jr., Seminole, FL (US); Joepert R. Lim, Palm Harbor, FL (US)

(73) Assignee: Linvatec Corporation, Largo, FL (US)

( * ) Notice: Subject to any disclaimer, the term of this patent is extended or adjusted under 35 U.S.C. 154(b) by 1864 days.

(21) Appl. No.: 10/072,235

(22) Filed: Feb. 7, 2002

(65) Prior Publication Data

US 2003/0149424 A1    Aug. 7, 2003

(51) Int. Cl.
*H01M 2/10* (2006.01)

(52) U.S. Cl. .............................. 429/97; 429/96; 429/99; 429/100

(58) Field of Classification Search ........................ None
See application file for complete search history.

(56) References Cited

U.S. PATENT DOCUMENTS 4,160,857 A * 7/1979 Nardella et al. ............... 429/97

\* cited by examiner

*Primary Examiner*—Patrick Ryan
*Assistant Examiner*—Cynthia Lee
(74) *Attorney, Agent, or Firm*—Gene Warzecha (57) ABSTRACT

A method and apparatus for enabling the use of a non-sterile battery with a sterile surgical instrument. The sterile transfer container has a tubular body with a closed distal end and an open proximal end. The container is provided with a cover and a locking mechanism for locking the cover to the body. The container is adapted to be attached to a surgical instrument in such a way that the latch assembly is prevented from opening until the container is removed from the instrument.

24 Claims, 10 Drawing Sheets

STERILE TRANSFER BATTERY CONTAINER

BACKGROUND OF THE INVENTION

1. Field of the Invention

The invention generally relates to surgical powered instruments. More particularly, the invention relates to battery operated surgical powered instruments. Still more particularly, the invention relates to methods and devices which enable the use of non-sterile rechargeable batteries with sterile surgical instruments.

2. Description of the Prior Art

In order to enable the use of rechargeable non-sterile batteries in sterile surgical instruments, users employ a known "sterile transfer" technique. While possibly known by other names, this technique generally entails the sterilization and use of a sterile battery container to be attached to a sterile powered instrument. The sterilized container is held in a sterile field (by a scrub nurse, for example) and is shielded by a sterile shroud. A non-sterile, charged battery (held by a circulating nurse, for example) is placed into the sterilized container with care so as not to contaminate the already sterilized container. The shroud is then removed by the circulating nurse and the sterilized container is closed by the scrub nurse and attached to the instrument. The container hermetically encloses the battery and has its own exterior terminals which are connected to the battery terminals and through which the instrument is powered.

The sterilized container must be closed and must stay closed during the surgical procedure. Due to the vibrations associated with the powered surgical instruments, it sometimes occurs that known designs of sterile transfer systems become open (thus exposing the non-sterile battery) or otherwise fail (by, for example, the sterilized container becoming detached from the instrument).

Accordingly, it is an object of this invention to produce a sterile transfer system with increased security from failure by exposure of non-sterile components or by premature disassembly.

It is also an object of this invention to produce a locking system for locking the sterilization container of a sterile transfer system.

It is an additional object of this invention to produce a sterile transfer locking system which interacts with the instrument to which the sterile transfer container is attached, thereby assuring that the locking system will not open while the container is attached to the instrument.

SUMMARY OF THE INVENTION

These and other objects of this invention are achieved by the preferred embodiment disclosed herein. In one aspect, the invention comprises a sterile transfer container comprising a tubular, cup-shaped body having an axis, a closed distal end and an open proximal end. The container also comprises a cover for releasably enclosing the proximal end and a locking means for locking the cover to the body. The locking means comprises an elongated member extending exteriorly of the body between the distal and proximal ends of the body in general parallel alignment with the axis. The elongated member has a proximal end and a distal end and a latching means is affixed to the distal end. The latching means is for selectively engaging a detent on the distal end of the body. The proximal end of the elongated member is secured to a lateral support member adjacent the cover and a releasable closing bias means is interposed between the cover and the lateral support member for urging the latching means against the detent means and the lateral support member against the cover, thus creating a compressive force between the cover and the body when the cover is locked.

In another aspect, the invention comprises the combination of a sterile transfer container, such as that described above, with a surgical instrument to be powered by the battery contained within the container. In such a combination, the sterile transfer container further comprises a terminal means extending through its body for electrically communicating with the battery terminals of a battery within the container, and an instrument attaching means adjacent said terminal means for attaching the tubular body to the instrument. A latch means is provided on the container to cooperate with a recess in the instrument in order to secure the attachment of the container to the instrument. The surgical instrument has a receiving means for mateably engaging the instrument attaching means and is adapted to be joined to the container in such a way that a portion of the instrument will block the latching means to prevent it from disengaging from the detent until the user decides to remove the container from the instrument by releasing the latch means on the container.

In a broader aspect the invention may be embodied in a sterile transfer container, and method of using same, which is adapted to receive a battery which can be enclosed with a movable cover. Such a container could be provided with a variety of different latch means for selectively latching the cover to the body and a variety of different lock means to secure the latch means to prevent its release.

DESCRIPTION OF THE PREFERRED EMBODIMENT

Figure 1:
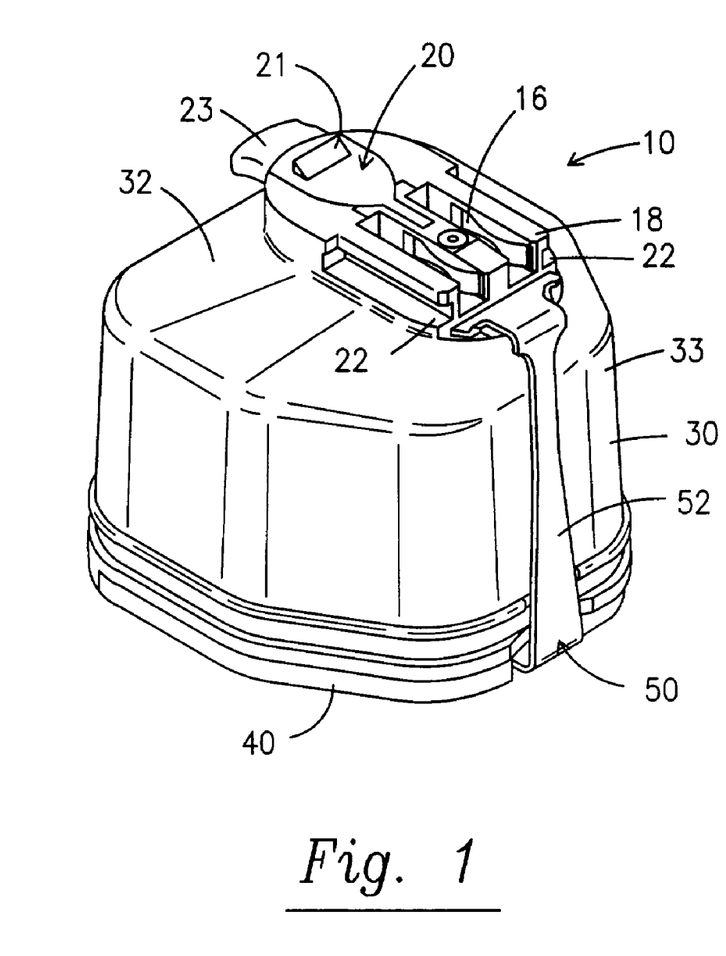
FIG. 1 is a front perspective view of a sterile transfer container, constructed in accordance with the principles of this invention showing the container in a closed configuration.
Figure 2:
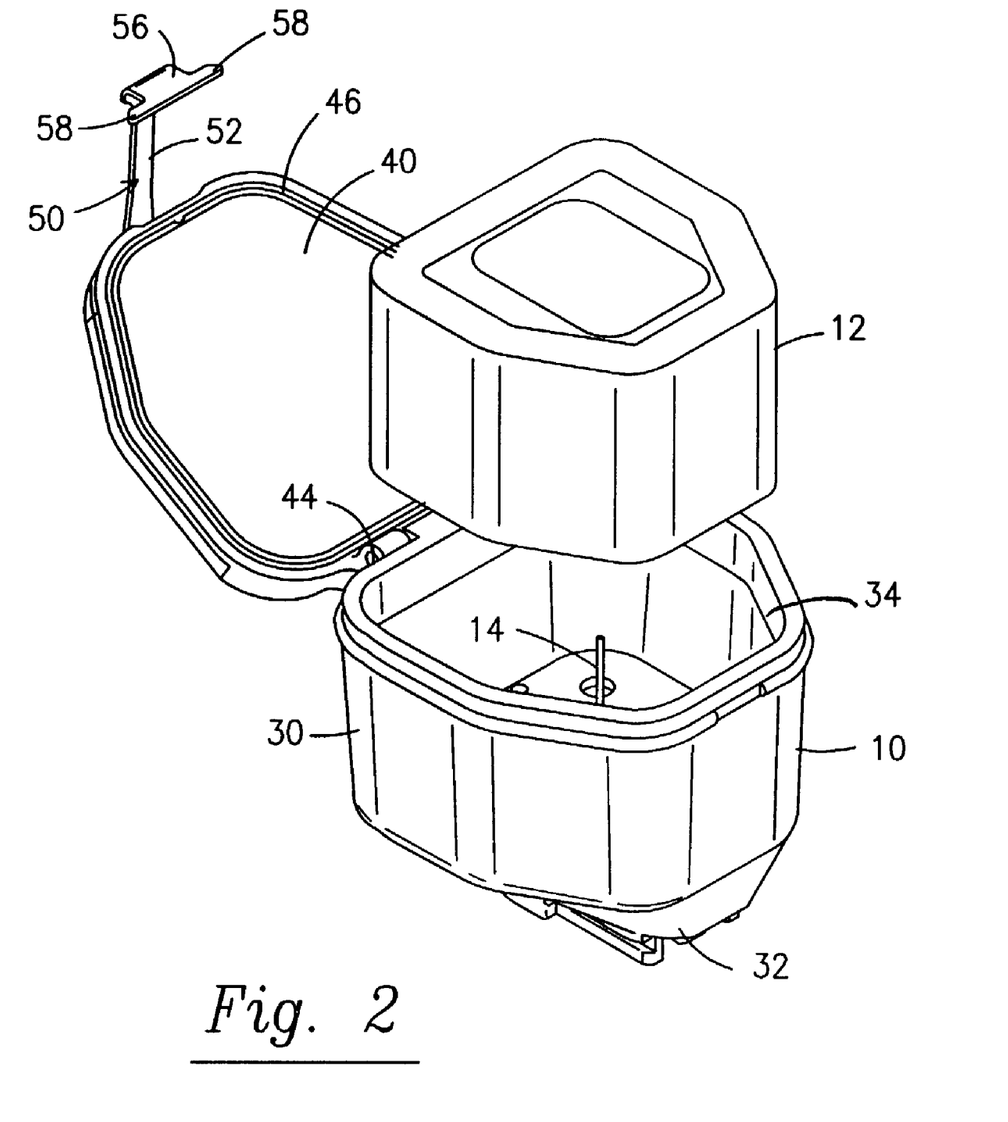
FIG. 2 is an inverted and rotated view of FIG. 1 showing the sterile transfer container in an open configuration and showing a battery which is designed for use with the container.
Figure 3:
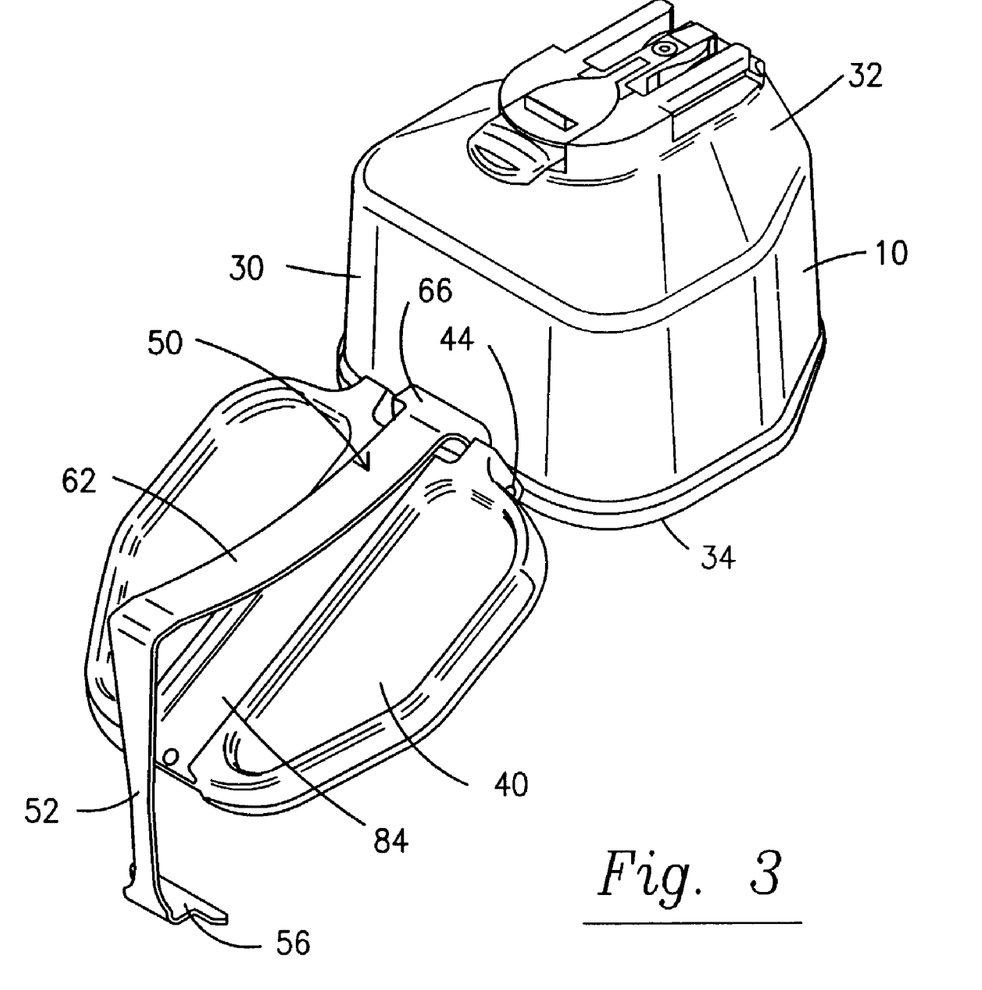
FIG. 3 is a rear perspective view of the sterile transfer container of FIG. 1 showing it in an open configuration.
Figure 9:
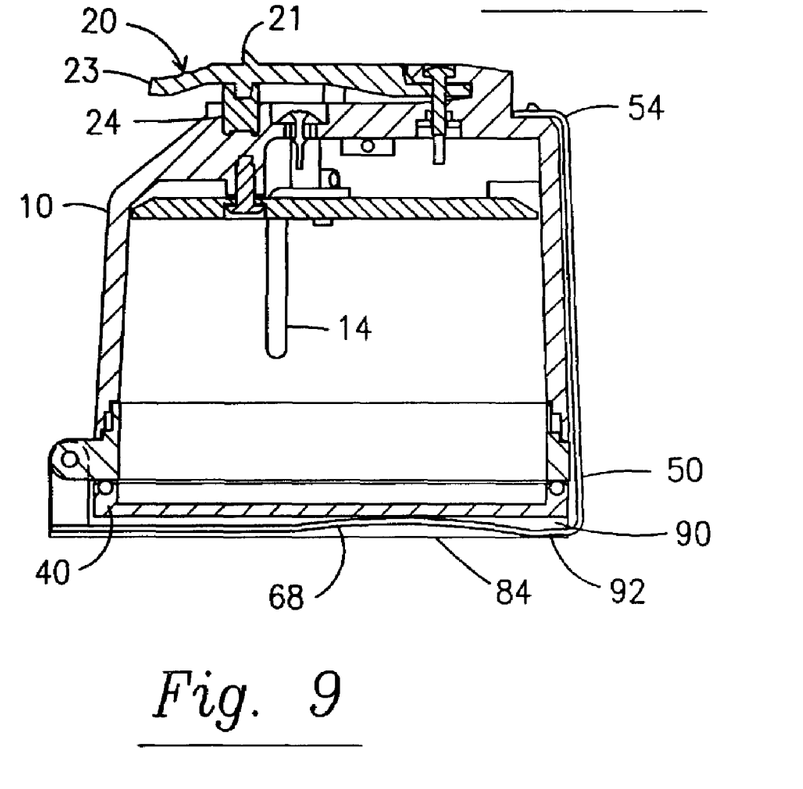
FIG. 9 is a cross-section of FIG. 8 taken along the lines 9-9, showing an empty container.

Referring now to the drawings, there is a shown a sterile transfer container 10 constructed in accordance with the principles of this invention. Container 10 is designed to hermetically enclose battery or battery pack 12 (best seen in FIG. 2) within a sterile environment since the battery itself is not intended to be sterilized when sterile transfer container 10 is used. The interior of sterile transfer container 10 is provided with positive and negative electrical terminals 14 (only one of which is visible in FIG. 2) which are received within complementary sockets (not shown) in battery 12. Terminals 14 are appropriately electrically connected to positive and negative exterior terminals 16 on the exterior of sterile transfer container 10. Container 10 further comprises mounting means 18 and spring loaded, pivotable latching mechanism 20 in order to enable container 10 to be securely attached to a powered surgical instrument 70, best seen in FIG. 7. As best seen in FIG. 9, latching mechanism 20 has a ramped latch 21 on a movable lever 23 which is biased upwardly by spring 24. Moving lever 23 downwardly (in FIG. 7) will release latch 21 from its corresponding recess.

Figure 5:
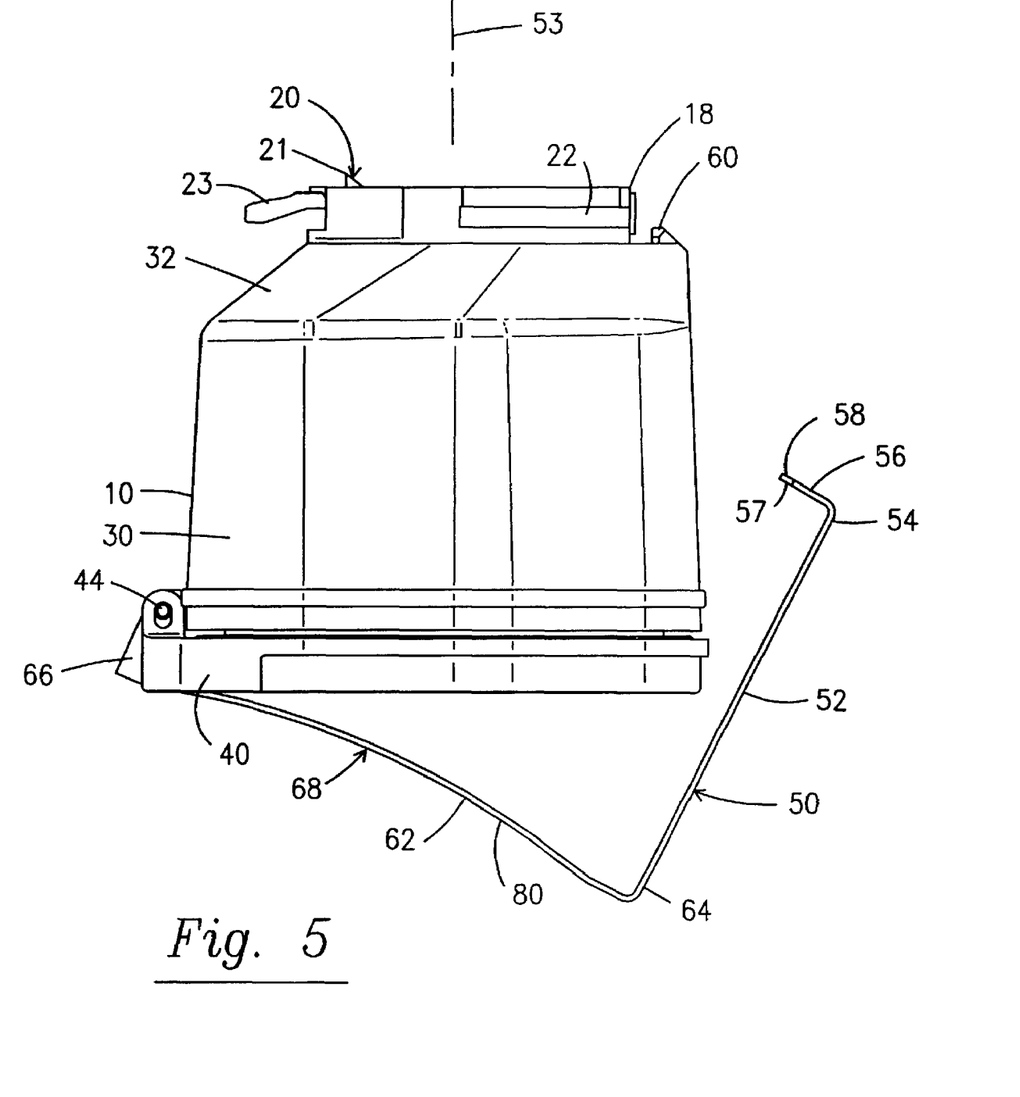
FIG. 5 is a side elevation view of the sterile transfer container in an unlocked configuration.

Mounting means 18 is provided with parallel grooves 22 (best seen in FIG. 5) in order to enable container 10 to be slidably attached to complementary ribs (not shown) in the bottom of surgical handpiece 70. Once the ribs are fully seated in the grooves, latching mechanism 20 engages a recess to keep container 10 attached to the handpiece.

Sterile transfer container 10 comprises a tubular or hollow body 30, a closed distal end 32 and an open proximal end 34. Distal end 32 has a periphery at which it is joined to a peripheral wall 33. Open end 34 is able to be selectively closed by a cover 40 which in the preferred embodiment is hingedly attached to body 30 by hinge 44. The peripheral junction between cover 40 and open end 34 is sealed with gasket 46 in order to ensure that the interior of sterile transfer container 10 is hermetically sealed when the cover is closed and locked so that the non-sterile battery 12 will be isolated from the exterior of the container during its use with a powered surgical instrument. In the preferred embodiment tubular body 30 is a generally rectilinear body with rounded edges. It will be understood, however, that tubular body 30 is generally cup-shaped with a peripheral wall which could be cylindrical or substantially cylindrical or could be formed in a variety of shapes.

Cover 40 is able to be locked in place by locking mechanism 50. Locking mechanism 50 comprises an elongated member 52 extending longitudinally between the distal and proximal ends of container 10. As will be understood, locking mechanism 50 serves to lock cover 40 to body 30 by exerting a distally (i.e. upwardly as viewed in FIGS. 1, 4, 7, 9 and 10) directed force pressing cover 40 against open end 34. Elongated member 52 extends longitudinally along the exterior of tubular body 30, generally parallel to axis 53 when the cover is locked. Member 52 has at its distal end 54 a laterally extending member 56 which is provided at its distal end 57 with a pair of transverse latching members 58. When cover 40 is closed and locked, latching members 58 are received adjacent to a pair of spaced apart detent shoulders 60 which extend upwardly from the distal end 32 of container 10 at a point adjacent the periphery of distal end 32. When locking mechanism 50 is so locked, lateral support member 62 is said to be in locking engagement with cover 40. Latching members 32 are retained by detent shoulders 60 until the locking mechanism is unlocked as will be understood below.

Locking mechanism 50 further comprises a lateral support member 62 joining the proximal end 64 of elongated member 52 to a transverse hinge connector 66. While hinge connector 66 is pivotably joined to the same hinge 44 to which cover 40 is connected, the cover is movable about hinge 44 independently of the latch assembly 68 made up of hinge connector 66, lateral support member 62, elongated member 52, laterally extending member 56 and transverse latching members 58. In the preferred embodiment latch assembly 68 is a unitary member although it will be understood that it could be formed of component parts joined together. Latch assembly 68 and all other components of sterile transfer container 10 are made of suitable biocompatible materials which can withstand the various sterilization processes to which container 10 may be subjected.

Figure 6:
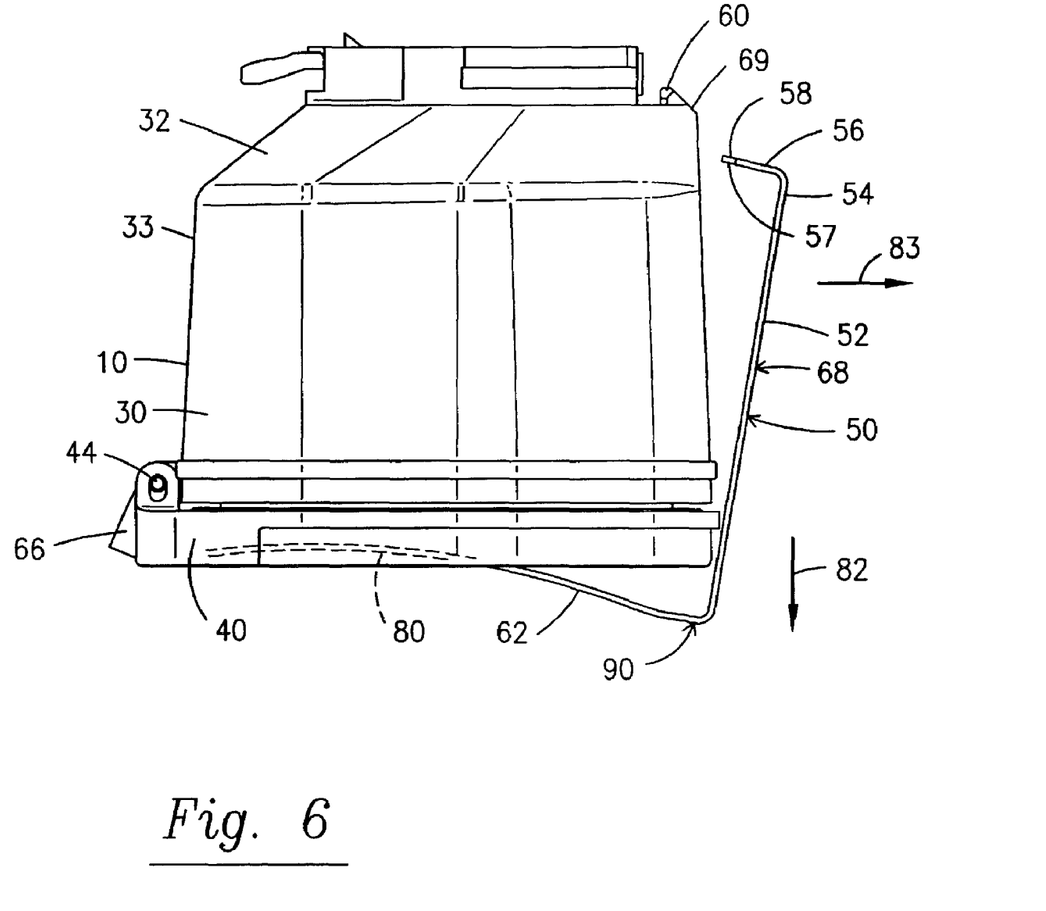
FIG. 6 is a side elevation view of the sterile transfer container in an alternate unlocked configuration.

Lateral support member 62 is formed of a somewhat resilient material and is, in the preferred embodiment, pre-bent at point 80 by a predetermined amount so that in the normal, unbiased configuration of latch assembly 68 (shown in FIGS. 5 and 6) elongated member 52 is moved in a proximal direction 82 (i.e. downwardly and laterally outwardly as best seen in FIG. 6) relative to where it would be situated without the bend in member 62. In the preferred embodiment latch assembly 68 (and, therefore, support member 62) is formed of stainless steel.

The operation of locking mechanism 50 may now be described. When cover 40 is closed, latch assembly 68 is pivoted about hinge 44 to the configuration shown in FIG. 6. The pre-bent point 80 causes the distal end of support member 62 (i.e. right side of member 62 as shown in FIG. 6) to be spaced from cover 40 while the proximal end of support member 62 (i.e. left side in FIG. 6) remains closer to the cover. A user can now lock cover 40 to tubular body 30 by pushing latch assembly 68 as shown at 92 to thereby move elongated member 52 and lateral member 56 upwardly (FIG. 6). Engagement of latching members 58 with detent members 60, i.e. the locked position shown in FIGS. 4 and 9, will be achieved if the user pushes distal end 54 laterally causing laterally extending member 56 and latching members 58 to mildly bend upwardly as they ride up ramp 69 until they drop behind detents 60, best seen in FIG. 4. The resiliency of latch assembly 68 produces a spring force which causes it to attempt to return it to its unbiased (i.e. open) configuration shown in FIGS. 5 and 6, thereby pulling latching members 58 down against distal end 32 and against detent members 60, thus exerting an upward force against cover 40. The spring force created by the pre-bent lateral support member 62 operates together with the engagement of latching members 58 and detents 60 to produce a compressive force between body 30 and cover 40. Alternatively, it will be understood that the compressive spring force could be provided by a separate spring (not shown) interposed between cover 40 and lateral support member 62 urging these elements away from each other. As an additional alternative, it will be understood that the compressive spring force could be provided by the inherent resiliency of lateral support member 62 without a pre-bend. In such a configuration a straight, non-bent lateral support member could be used with a central fulcrum formed in cover 40 (similar to point 98 in FIG. 10).

Cover 40 is provided with channel 84 which receives lateral support member 62. Channel 84 is wide enough to receive member 62 and, as best seen in FIGS. 4 and 9, it is deep enough to enable cover 40 of a closed sterile transfer container 10 to be placed on a surface without causing the surface to contact latch assembly 68, thereby inadvertently unlocking the cover by pushing up on elongated member 52.

Figure 4:
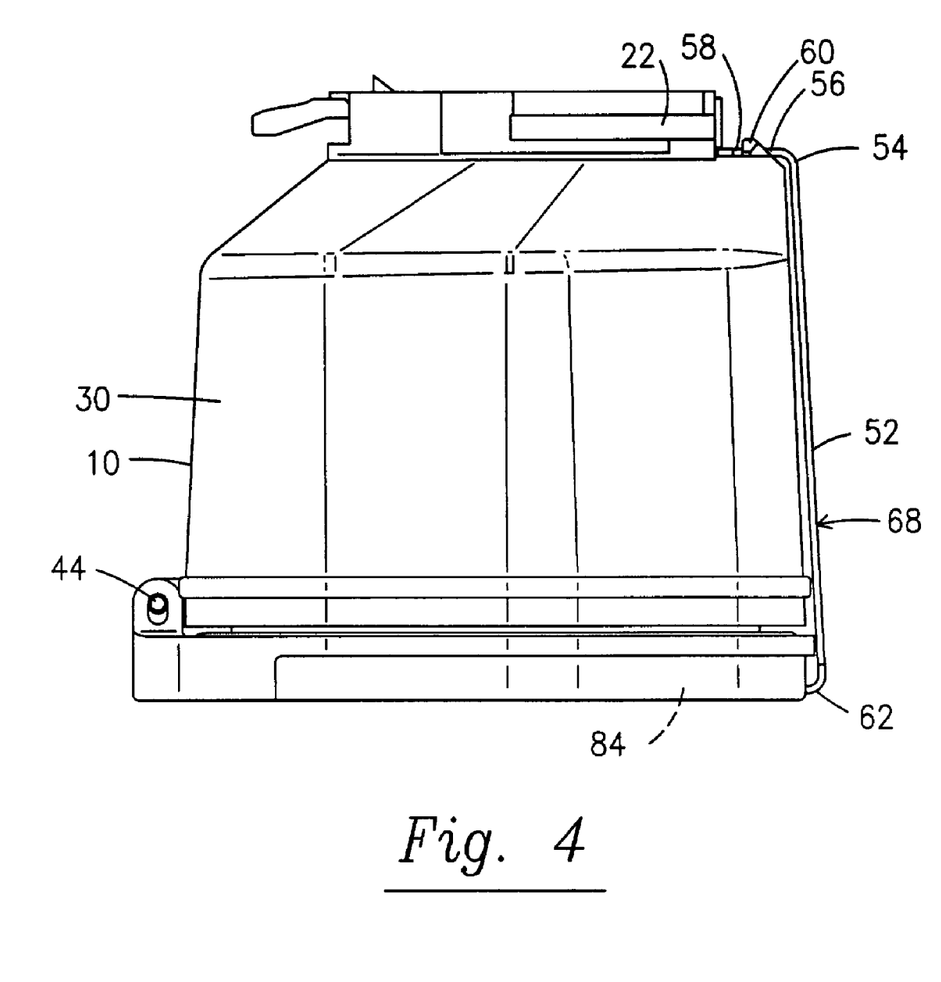
FIG. 4 is a side elevation view of the sterile transfer container of FIG. 1.

The degree to which lateral support member 62 is pre-bent is such that even in the locked position shown in FIGS. 4 and 9 there is a gap 90 between the bottom of channel 84 and member 62. This gap enables a user to unlock locking mechanism 50 by pushing lateral support member 62 at point 92 to thereby move latching members 58 upwardly and out of engagement with detent members 60. This automatically causes distal end 54 to move laterally thereby returning latch assembly 68 to its unbiased form (shown in FIGS. 5 and 6) so subsequent release at point 92 will enable latch assembly 68 to be hingedly moved about hinge 44. The cover 40 may now be opened.

It is noted that the attachment of latch assembly 68 at hinge 44, at a point diametrically opposed from elongated member 52 results in lateral support member 62 extending entirely across cover 40. The spring tension imparted to latch assembly 68 by the pre-bend at point 80 causes the latching members 58 to pull against detents 60 and thereby apply a closing force to cover 40 on the right side of FIG. 9. Hinge 44 and hinge connector 66 produce a closing force on the left side of FIG. 9.

Figure 7:
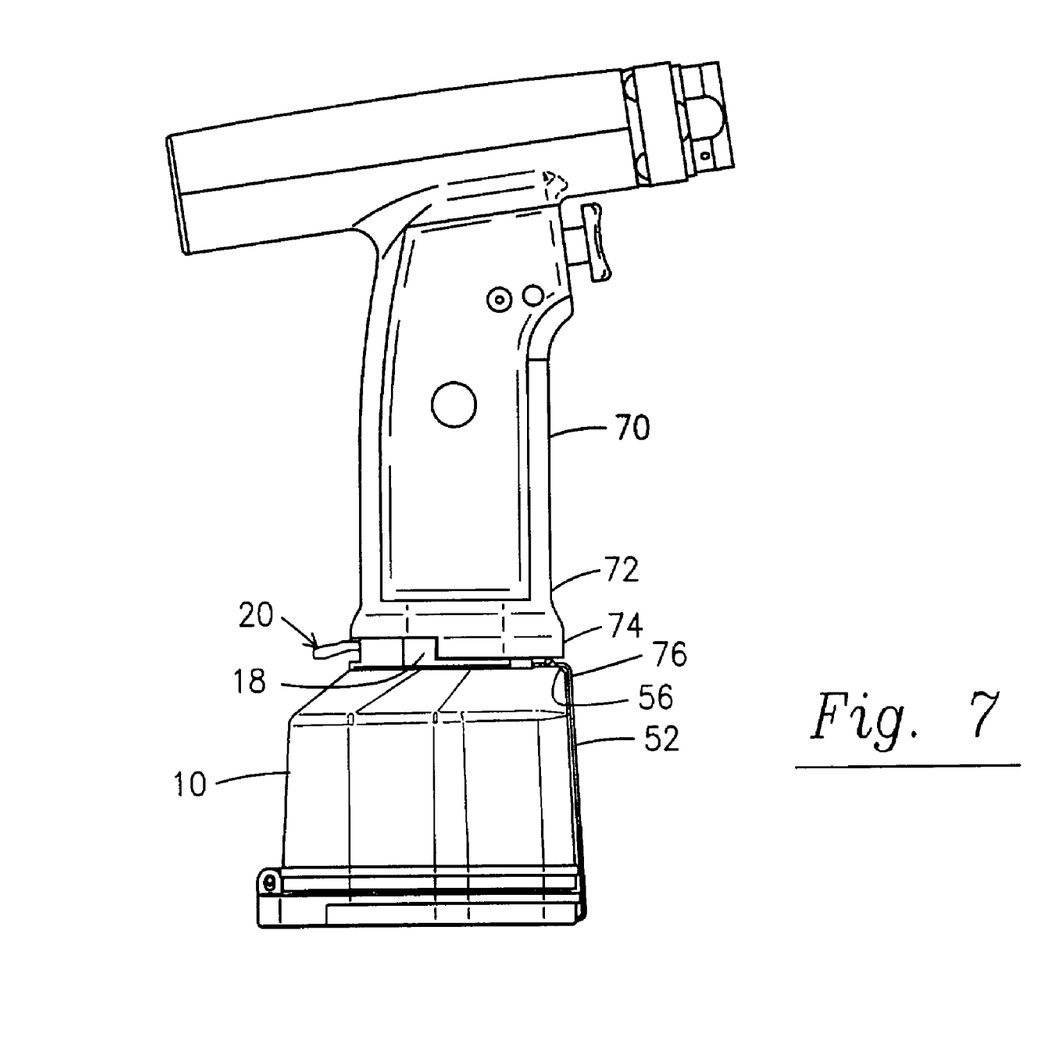
FIG. 7 is a side elevation view of the sterile transfer container attached to a surgical powered instrument.
Figure 8:
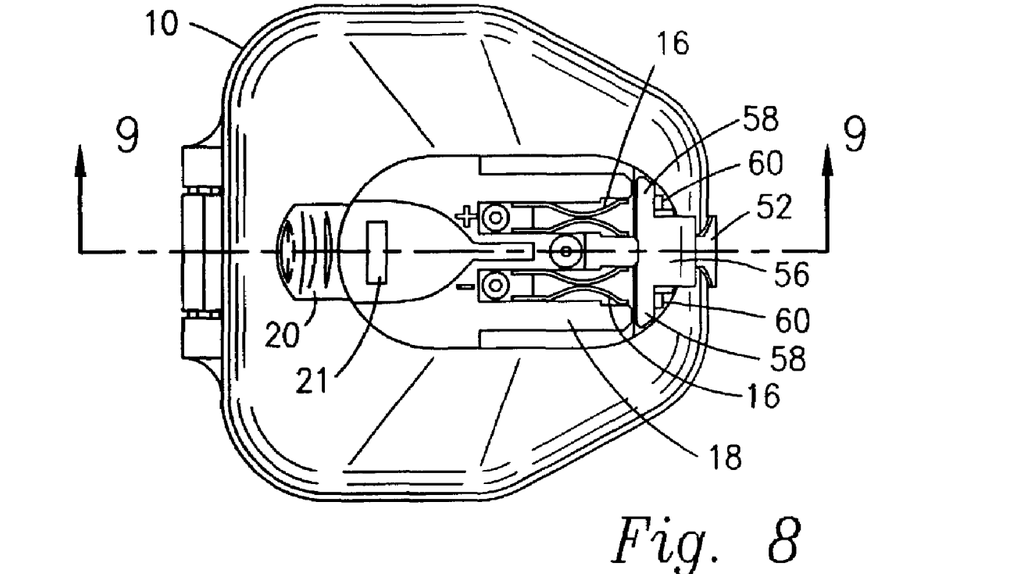
FIG. 8 is a top plan view of FIG. 1.

As best seen in FIG. 7, sterile transfer container 10 is attachable to a variety of surgical instruments, one of which is shown as instrument 70. The handle 72 of instrument 70 is a pistol-grip style and has a bottom end which is adapted to slidably engage mounting means 18. Handle 72 is provided with ribs (not shown) to engage grooves 22 and with a recess (not shown) to engage latch 21. When latch 21 is engaged in its recess, the bottom front portion 74 of handle 72 will be approximately aligned with the front 76 of tubular body 30 and will be above laterally extending member 56. The bottom surface of front portion 74 may abut the top of the detents 60 and/or latching members 58, or may be separated therefrom by a small gap. The gap between the bottom of the handle and latching members 58 and detents 60 is small enough such that it will prevent disengagement of the latching members from the detents so that the sterile transfer container 10 cannot open during use of the instrument until latch 20 is released by moving lever 23 downwardly thereby enabling the container to be slidably moved out of engagement with instrument 70. It will be understood that latch 20 and its corresponding recess could be reversed so that a movable latch could be situated on the instrument with the mateable recess situated on the sterile transfer container.

Figure 10:
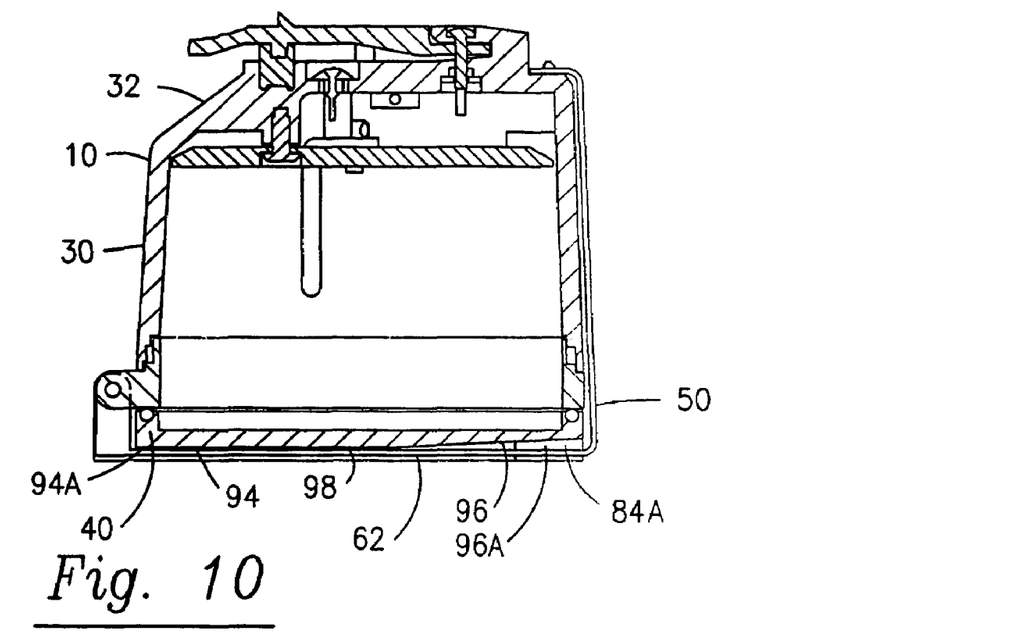
FIG. 10 is a cross-section view of an alternate embodiment of the sterile transfer container.

In an alternate embodiment shown in FIG. 10, the closing force with which latch assembly 68 presses cover 40 against tubular body 30 is enhanced by modifying channel 84 into channel 84A having two oppositely oriented ramps. Thus, the surface of channel 84A comprises left ramp 94 and right ramp 96 each sloping away from distal end 32 toward a central point 98 to provide a centrally located contact surface on cover 40 for contacting lateral support member 62. The central location evenly distributes the closing force around the periphery of cover 40. In a preferred embodiment, left ramp 94 has a small gap 94A between it and lateral support member 62, while right ramp 96 has a larger gap 96A between it and lateral support member 62. Gap 96A is greater than gap 94A to enable the lateral support member 62 to be deformed momentarily, enough to disengage latching members 58 from detent means 60.

Figure 11:
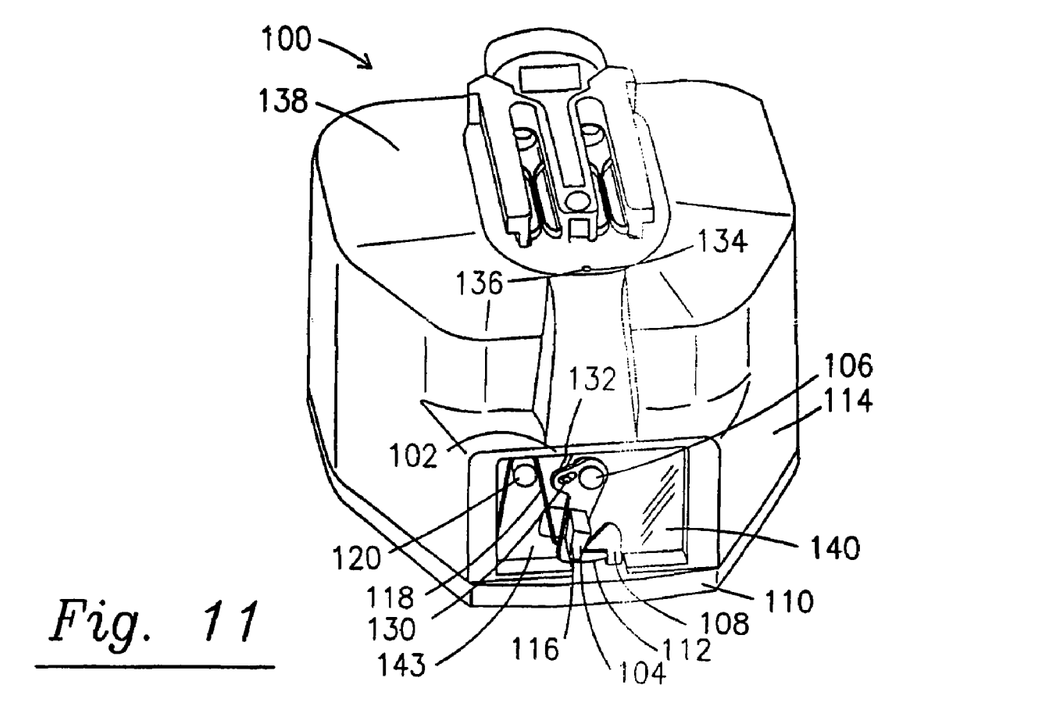
FIG. 11 is a front perspective view of another alternate embodiment of the sterile transfer container.
Figure 12:
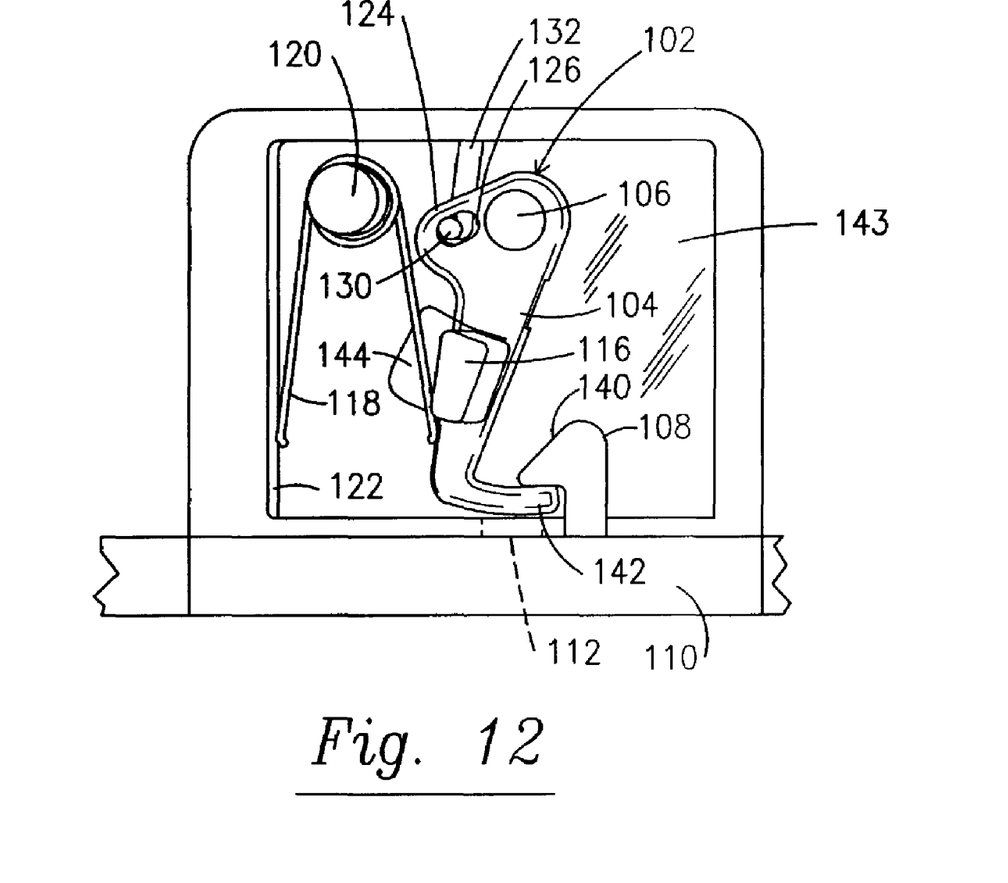
FIG. 12 is an exploded view of a portion of FIG. 11.

FIGS. 11 and 12 show another alternate embodiment of the invention in the form of sterile transfer container 100 which is identical to container 10 in all respects except for the locking mechanism. While both container 10 and container 100 have a locking mechanism which is prevented from opening when the container is attached to a surgical instrument, locking mechanism 50 used on container 10 may be deemed an example of a direct lock and locking mechanism 102 used on container 100 may be deemed an example of an indirect lock. The direct aspect lies in the direct engagement of a latch (i.e. latching members 58) by the surgical instrument used with container 10. The indirect aspect lies in the indirect engagement of a latch used on container 100 as will be understood below.

Locking mechanism 102 comprises a movable latching member 104 pivotable about transverse pin 106 and selectively engageable with detent hook 108. Detent 108 is fixedly attached to cover 110 and extends through a slot 112 in container body 114. Cover 110 is pivotable about a hinge on the side of body 114 hidden from view in FIG. 11 (similarly to cover 40). Latching member 104 is provided with a handle 116 to enable a user to pivot it about pin 106 into either an open position, disengaged from detent hook 108, or a closed position as shown in FIGS. 11 and 12. A spring 118, mounted on transverse pin 120 and compressed between member 104 and transverse wall 122, biases member 104 into the closed position.

Latching member 104 further comprises a lateral extension 124 having an aperture 126 for the purpose of applying a pivoting force to member 104. Aperture 126 receives the proximal end 130 of an elongated securing rod 132. End 130 may be engaged with aperture 126 by simply being bent transversely to the axis of rod 132, or may be otherwise attached to latching member 104. Rod 132 extends and is movable within a channel (not shown) in the wall of container body 114 so that its distal end 134 can protrude from aperture 136 in the distal surface 138 of container 100.

It will be understood that when cover 110 is pushed in to the closed position detent hook 108 will, by virtue of ramp 140, pivot latching member 104 counterclockwise (as viewed in FIG. 12). Rod 132 will thus be caused to move upwardly and, unless a surgical instrument or other obstruction blocks distal end 134, end 134 will also move upwardly. When ramp 140 clears the hook 142 of member 104, spring 118 will urge member 104 clockwise, thus pulling down rod 132 and its distal end 134. In this position, end 134 is preferably flush with the surface of distal surface 138. It will be understood that if such a closed and locked container 100 is attached to a surgical instrument (similarly to the way container 10 is attached in FIG. 7), the instrument will block upward motion of end 134 and prevent upward movement of rod 132, thus holding latching member 104 in the locked position.

In the embodiment shown in FIGS. 11 and 12 locking mechanism 102 is situated within a recess 140 in the wall of body 114. Recess 140 is covered by a wall section 142 which smoothly blends with the outer surface of the wall of body 114 and which has an aperture 144 through which handle 116 extends. In the drawings wall section 142 is shown to be transparent.

A further distinction between locking mechanism 50 and 102 is that the former has movable components on the cover side of the sterile transfer container while the latter has movable components on the body side.

While the preferred embodiments utilize terminals extending through the body of the sterile transfer container, as opposed to through the cover, it will be understood that the terminals could extend through the cover as well. Therefore, when it is stated herein that terminals extend through the body of the container, it will be understood that such use of the term "body" is meant to include the cover. Additionally, it will be understood that the mounting means could be situated on the cover along with the terminals. Appropriate modifications of the invention could be made to secure such an embodiment to a surgical instrument. Indeed, the terminals and mounting means could be placed anywhere on the sterile transfer container and be adapted to operate with an appropriate compatible instrument as taught herein.

The preferred embodiments operate by blocking motion of a latching member or an intervening securing member with a predetermined portion of the surgical instrument. Optionally, such blocking could be effected by another component (strap, bar, etc.) which could be attached to both the instrument and the sterile transfer container.

It will be understood by those skilled in the art that numerous improvements and modifications may be made to the preferred embodiment of the invention disclosed herein without departing from the spirit and scope thereof.

What is claimed is:

1. A sterile transfer container for containing a battery having electrical terminals for powering a surgical instrument comprising:
   a tubular body having an axis, a closed distal end and an open proximal end, said distal end having a detent means for being engaged by a member;
   terminal means extending through said tubular body for electrically communicating with the battery terminals of a battery retained within said body;
   a cover for releasably enclosing said open proximal end; and
   locking means for locking said cover to said body, said locking means comprising:
      an elongated member extending exteriorly of said body between said distal and proximal ends of said body, in general parallel alignment with said axis, said elongated member having a proximal end and a distal end;
      a latching means affixed to said distal end of said elongated member, said latching means for selectively engaging said detent means on said distal end of said body;
      a lateral support member for selective locking engagement with said cover, said lateral support member secured transversely to said proximal end of said elongated member; and
      releasable closing bias means for urging said latching means against said detent means and said lateral support member against said cover when said cover is locked, said closing bias means interposed between said elongated member and said cover.

2. A sterile transfer container according to claim 1 wherein said tubular body has a peripheral wall wherein said detent means is adjacent said peripheral wall and said detent means comprises at least one longitudinally extending shoulder situated on said distal end of said tubular body adjacent the periphery of said distal end; and
   wherein said latching means comprises a member affixed to said distal end of said elongated member and laterally extending therefrom toward said axis.

3. A sterile transfer container according to claim 1 wherein said lateral support member is resilient and wherein said releasable closing bias means comprises:
   a predetermined bend in said lateral support member causing said latching means to move proximally away from said detent means when said locking means is not biased, said bend thereby creating, when said latching member is in engagement with said detent, a compressive force between said body and said cover.

4. A sterile transfer container according to claim 2 wherein said lateral support member is resilient and wherein said releasable closing bias means comprises:
   a fulcrum means extending proximally from said cover for deforming said lateral support member when said cover is locked.

5. A sterile transfer container according to claim 1 wherein said lateral support member is attached to said body at a point diametrically opposite said elongated member.

6. A sterile transfer container according to claim 1 wherein said cover is hingedly joined to said tubular body at a point diametrically opposed from said elongated member and wherein said lateral support member is hingedly joined at said point.

7. A sterile transfer container according to claim 5 wherein said lateral support member is hingedly movable about said point independently of said cover.

8. A sterile transfer container according to claim 1 further comprising:
   instrument attachment means adjacent said terminal means for attaching said tubular body to an instrument to be powered by a battery within said tubular body; and
   movable latch means for securing attachment of said tubular body to said instrument.

9. A sterile transfer container according to claim 8 in combination with a surgical instrument comprising receiving means for mateable engagement with said instrument attaching means wherein said detent means and said latching means are adapted to be blocked, when said cover is locked and when said instrument is attached to said instrument attaching means, to prevent disengagement of said latching means from said detent means until said latch means is released.

10. In combination a sterile transfer container for retaining a battery therein and a surgical instrument for being powered by the battery, said sterile transfer container comprising:
    a tubular body having an axis, a closed distal end and an open proximal end, said distal end having a detent means for being engaged by a member;
    terminal means extending through said tubular body for electrically communicating with the battery terminals of a battery retained within said body;
    instrument attaching means adjacent said terminal means for attaching said tubular body to said instrument;
    a cover for releasably enclosing said open proximal end; and
    locking means for locking said cover to said body, said locking means comprising:
       an elongated member extending exteriorly of said body between said distal and proximal ends of said body, in general parallel alignment with said axis, said elongated member having a proximal end and a distal end;
       a latching means affixed to said distal end of said elongated member, said latching means for selectively engaging said detent means on said distal end of said body;
       a lateral support member for selective locking engagement with said cover, said lateral support member secured transversely to said proximal end of said elongated member;
       releasable closing bias means for urging said latching means against said detent means and said lateral support member against said cover when said cover is locked, said closing bias means interposed between said elongated member and said cover;
    and said surgical instrument comprising:
       receiving means for mateable engagement with said instrument attaching means; and
       blocking means for preventing disengagement of said latching means from said detent means when said sterile transfer container is attached to said instrument.

11. The combination according to claim 10 further comprising movable latch means for securing attachment of said tubular body to said instrument and wherein said blocking means comprises a predetermined portion of said instrument which prevents disengagement of said latching means from said detent means until said latch means is released and said tubular body is detached from said instrument.

12. A method for securing a sterile transfer container, holding a battery, to a surgical instrument comprising the steps of:

providing a sterile transfer container comprising:
a tubular body having an axis, a closed distal end and an open proximal end, said distal end having a detent means for being engaged by a member;
terminal means extending through said tubular body for electrically communicating with the battery terminals of a battery retained within said body;
instrument attaching means adjacent said terminal means for attaching said tubular body to said instrument;
movable latch means for securing attachment of said tubular body to said instrument;
a cover for releasably enclosing said open proximal end; and
locking means for locking said cover to said body, said locking means comprising:
an elongated member extending exteriorly of said body between said distal and proximal ends of said body, in general parallel alignment with said axis, said elongated member having a proximal end and a distal end;
a latching means affixed to said distal end of said elongated member, said latching means for selectively engaging said detent means on said distal end of said body;
a lateral support member for selective locking engagement with said cover, said lateral support member secured transversely to said proximal end of said elongated member;
releasable closing bias means for urging said latching means against said detent means and said lateral support member against said cover when said cover is locked, said closing bias means interposed between said elongated member and said cover;
providing on said instrument a receiving means for mateably engaging said attaching means;
attaching said receiving means to said attaching means; and
blocking said latching member with a predetermined portion of said instrument to prevent said latching means from becoming disengaged from said detent means while said container is attached to said instrument.

13. A method according to claim 12 wherein said instrument comprises a pistol-grip handle adjacent said receiving means, and wherein said blocking step is accomplished by a predetermined portion of said handle.

14. A sterile transfer container for containing a battery having electrical terminals for powering a surgical instrument comprising:
a hollow body having a closed distal end and an open proximal end;
terminal means extending through said body for electrically communicating with the battery terminals of a battery retained within said body;
a cover for releasably enclosing said open proximal end;
latch means for selectively latching said cover to said body and said body to said instrument;
and lock means for securing said latch means to selectively prevent its release;
instrument attachment means adjacent said terminal means for attaching said body to an instrument to be powered by a battery within said body; and
receiving means for mateable engagement with said instrument attaching means wherein detent means and said latch means are adapted to be blocked, when said cover is locked and when said surgical instrument is attached to said instrument attachment means, to prevent disengagement of said latch means from said detent means until said latch means is released.

15. A sterile transfer container according to claim 14 wherein said cover is hingedly joined to said body at a point diametrically opposed from said latch means.

16. A sterile transfer container according to claim 14 wherein said latch means comprises:
a fixed detent means on said body; and
a movable latching member attached to said cover and for selectively engaging said fixed detent means.

17. A sterile transfer container according to claim 13 wherein said latch means comprises:
a fixed detent means on said cover; and
a movable latching member attached to said body and for selectively engaging said fixed detent means.

18. In combination a sterile transfer container for retaining a battery therein and a surgical instrument for being powered by the battery, said sterile transfer container comprising:
a hollow body having a closed distal end and an open proximal end;
terminal means extending through said body for electrically communicating with the battery terminals of a battery retained within said body;
a cover for releasably enclosing said open proximal end;
latch means for selectively latching said cover to said body and said body to said instrument;
and lock means for securing said latch means to selectively prevent its release;
instrument attaching means adjacent said terminal means for attaching said body to an instrument to be powered by a battery within said body; and
receiving means for mateable engagement with said instrument attaching means wherein detent means and said latch means are adapted to be blocked, when said cover is locked and when said surgical instrument is attached to said instrument attachment means, to prevent disengagement of said latch means from said detent means until said latch means is released.

19. A method for securing a sterile transfer container, holding a battery, to a surgical instrument comprising the steps of:
providing a sterile transfer container comprising: a body having a closed distal end and an open proximal end;
terminal means extending through said body for electrically communicating with the battery terminals of a battery retained within said body;
a cover for releasably enclosing said open proximal end;
latch means for selectively latching said cover to said body; and lock means for securing said latch means to selectively prevent its release;
providing on said instrument a receiving means for mateably engaging said attaching means;
blocking said latch means to prevent said latch means from becoming released while said container is attached to said instrument
providing instrument attaching means adjacent said terminal means for attaching said body to an instrument to be powered by a battery within said body; and
attaching receiving means for mateable engagement with said instrument attaching means wherein detent means and said latch means are adapted to be blocked, when said cover is locked and when said surgical instrument is attached to said instrument attachment means, to prevent disengagement of said latch means from said detent means until said latch means is released.

20. A method according to claim 19 wherein said blocking step is effected by contiguous engagement of said latch means with a predetermined portion of said instrument.

21. A method according to claim 19 wherein said instrument comprises a pistol-grip handle adjacent said receiving means, and wherein said blocking step is accomplished by a predetermined portion of said handle.

22. In combination a sterile transfer container and a surgical instrument, said sterile transfer container adapted to receive a battery therein and adapted to be attached to said surgical instrument for powering said surgical instrument, said sterile transfer container and said surgical instrument each comprising respective, mateable engagement means for releasably attaching said sterile transfer container to said surgical instrument, said sterile transfer container comprising:
   a hollow body for containing a battery, said body having an opening through which a battery may be inserted:
   a cover for hermetically enclosing said battery within said body by selectively covering said opening;
   latch means for selectively latching said cover to said body and said body to said instrument;
   lock means for securing said latch means to prevent its release when said body is attached to said surgical instrument and said surgical instrument comprising:
   blocking means for preventing release of said lock means when said sterile transfer container is attached to said instrument
   instrument attaching means adjacent said terminal means for attaching said body to an instrument to be powered by a battery within said body; and
   receiving means for mateable engagement with said instrument attaching means wherein detent means and said latch means are adapted to be blocked. when said cover is locked and when said surgical instrument is attached to said instrument attachment means, to prevent disengagement of said latch means from said detent means until said latch means is released.

23. The combination of claim 22 wherein said latch means comprises a releasable latching member interposed between said cover and said body and wherein said lock means comprises a latching member and said detent means which are directly engaged by said surgical instrument to prevent motion thereof when said sterile transfer container and said instrument are attached to each other.

24. The combination of claim 22 wherein said latch means comprises a releasable latching member interposed between said cover and said body, and wherein said lock means comprises a securing means interposed between said latching member and said surgical instrument, said securing means having a proximal end attached to said releasable latching member and a distal end adapted to be selectively abutted against said surgical instrument when said sterile transfer container and said instrument are attached to each other, said abutment comprising indirect engagement of said surgical instrument with said latching member to prevent motion thereof when said sterile transfer container and said instrument are attached to each other.

* * * * *